(12) United States Patent
Benscoter et al.

(10) Patent No.: US 9,790,081 B2
(45) Date of Patent: Oct. 17, 2017

(54) MODULARIZED COMPONENTS ASSEMBLED FLUID DISPENSING NOZZLE

(71) Applicants: Richard Benscoter, Union, MO (US); John Sever, Pacific, MO (US); Darrell Vilmer, Florissant, MO (US); Roger Wiersma, Pacific, MO (US); Brian Wolff, Raytown, MO (US)

(72) Inventors: Richard Benscoter, Union, MO (US); John Sever, Pacific, MO (US); Darrell Vilmer, Florissant, MO (US); Roger Wiersma, Pacific, MO (US); Brian Wolff, Raytown, MO (US)

(73) Assignee: Husky Corporation, Pacific, MO (US)

( * ) Notice: Subject to any disclaimer, the term of this patent is extended or adjusted under 35 U.S.C. 154(b) by 475 days.

(21) Appl. No.: 14/121,162

(22) Filed: Aug. 8, 2014

(65) Prior Publication Data

US 2015/0007907 A1    Jan. 8, 2015

Related U.S. Application Data

(63) Continuation of application No. 12/932,880, filed on Mar. 9, 2011, now abandoned.

(60) Provisional application No. 61/340,995, filed on Mar. 25, 2010.

(51) Int. Cl.
| | | |
|---|---|---|
| *B65B 1/30* | (2006.01) | |
| *B67D 7/46* | (2010.01) | |
| *B67D 7/42* | (2010.01) | |
| *B67D 7/04* | (2010.01) | |

(52) U.S. Cl.
CPC ............. *B67D 7/46* (2013.01); *B67D 7/04* (2013.01); *B67D 7/42* (2013.01)

(58) Field of Classification Search
CPC .................................. B67D 7/46; B67D 7/04
See application file for complete search history.

(56) References Cited

U.S. PATENT DOCUMENTS

| | | | | |
|---|---|---|---|---|
| 3,273,609 | A | * | 9/1966 | Carder ............ B67D 7/50 |
| | | | | 141/206 |
| 3,352,332 | A | | 11/1967 | Swatek et al. |
| 4,378,824 | A | * | 4/1983 | Carder, Sr. ...... B67D 7/48 |
| | | | | 137/382.5 |
| 4,450,879 | A | | 5/1984 | Wood |
| 4,453,578 | A | | 6/1984 | Wilder |

(Continued)

*Primary Examiner* — Jason K Niesz
(74) *Attorney, Agent, or Firm* — Paul M Denk

(57) ABSTRACT

Modularized components assembled dispensing nozzle, including operating components in the category of a poppet valve assembly, an automatic shutoff device, a hand operating lever for providing a turn on or shutoff of the dispensing of fluid through the nozzle, and a connected spout that delivers fluid to the fill pipe and fuel tank for a vehicle or fluid accepting container. Each of the identified components having been redesigned for assembly in modularized form, such as a modular cartridge for the poppet valve, a modular cartridge for the automatic shutoff device, a modularized operating hand lever, and a spout and its gland and retaining nut that provide for high speed interconnection with the nozzle body, during assembly, or servicing. Each of these modularized components can be installed, during assembly of the manufactured nozzle, or can be replaced, out in the field, by a service person, as a modularized component or cartridge assembly.

5 Claims, 7 Drawing Sheets

(56) References Cited

U.S. PATENT DOCUMENTS

| | | | |
|---|---|---|---|
| 5,016,687 A | | 5/1991 | Kawamura |
| 5,067,533 A | * | 11/1991 | Carder, Sr. .............. B67D 7/50 141/206 |
| 5,127,451 A | | 7/1992 | Fink, Jr. et al. |
| 5,224,525 A | * | 7/1993 | Weichel ................... B67D 7/48 141/206 |
| 5,403,043 A | * | 4/1995 | Smet ................... F16L 37/2445 285/148.21 |
| 5,474,115 A | * | 12/1995 | Fink, Jr. ................... B67D 7/34 141/206 |
| 5,562,133 A | | 10/1996 | Mitchell |
| 5,577,538 A | | 11/1996 | Sunderhaus et al. |
| 6,394,139 B1 | | 5/2002 | Mitchell et al. |
| 6,585,014 B1 | | 7/2003 | Fink, Jr. |
| 6,698,471 B1 | * | 3/2004 | Carmack ................. B67D 7/50 141/206 |
| 2002/0074535 A1 | | 6/2002 | Fink, Jr. |
| 2006/0243348 A1 | | 11/2006 | Poli |
| 2011/0232803 A1 | | 9/2011 | Benscoter et al. |

\* cited by examiner

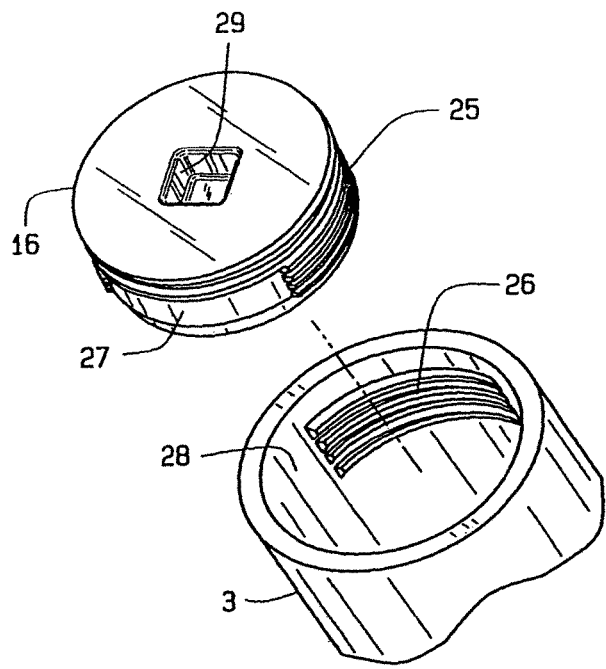
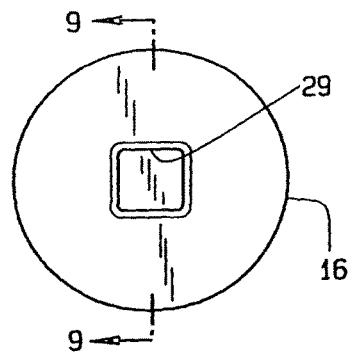
FIG. 8
FIG. 7
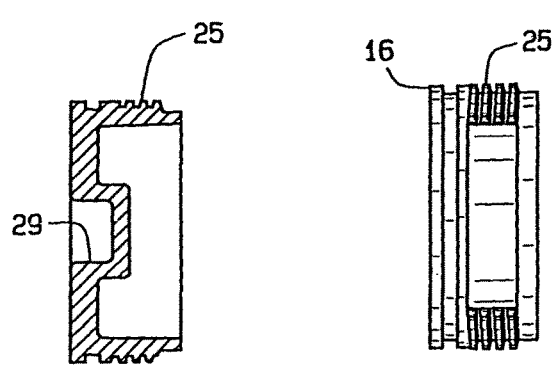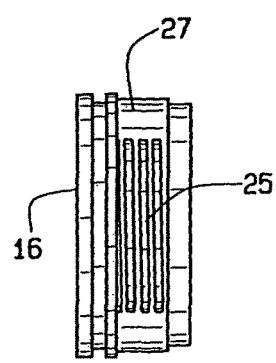
FIG. 9
FIG. 10
FIG. 11

MODULARIZED COMPONENTS ASSEMBLED FLUID DISPENSING NOZZLE

CROSS REFERENCE TO RELATED APPLICATION

This application is a continuation of U.S. patent application Ser. No. 12/932,880, which was filed on Mar. 9, 2011, which claimed priority to the provisional patent application having Ser. No. 61/340,995, having a filing date Mar. 25, 2010.

FIELD OF THE DISCLOSURE

This disclosure relates primarily to fluid or fuel dispensing nozzles, and more specifically pertains to a modularized components assembled fluid dispensing nozzle, wherein the detailed operative components of the nozzle such as its poppet valve assembly, the automatic shutoff assembly, and other components are designed and assembled as modularized components, and can be easily removed and replaced intact in their entirety, for purposes of service, cleaning, repair, or replacement.

BACKGROUND

This disclosure relates to a dispensing nozzle. Many nozzles have been designed, developed, patented, and used in the past, that incorporate the usual operating components, such as poppet valves, hand lever assemblies, automatic shutoff components, and various spout designs, and many of such prior developments have been undertaken by the assignee of the current disclosure herein, who has been in the business of manufacturing and marketing dispensing nozzles for many, many years. For example, the assignee's prior U.S. Pat. No. 5,127,451, upon a dispensing nozzle improvement, in its main embodiment, shows the balanced pressure type of nozzle, that does incorporate a poppet valve, an automatic shutoff and its diaphragm assembly, including an operating hand lever system, to provide for dispensing of fuel when the nozzle has been conveniently applied to the fill pipe of a gasoline tank for automobiles, and other machines. The United States patent to the same assignee, U.S. Pat. No. 5,474,115, shows a related style of poppet valve, and a shutoff assembly, for a nozzle, as can be noted. Most of these earlier nozzles, and the various components as identified that are fitted into their structure, require a complete assembly of these components for the nozzle, from a myriad of individual parts, which must be assembled into the nozzle body, during constructing of the nozzle. Or, if several of these components need servicing or cleaning in a well used fuel nozzle, these components must be individually removed, all the parts disassembled, in order to provide for servicing of the subject nozzle. This not only requires a service person of high engineering and mechanical skill, but is very time consuming to service such a used nozzle, frequently requiring a replacement of the entire dispensing nozzle, and returning the used nozzle back to the manufacturing plant, for rebuilding. Thus, one of the primary objects of the current disclosure is to provide for a modularization of select of these components for a nozzle, so that the service person, even in the field, can simply remove a poppet modularized component, or an automatic diaphragm operated shutoff component, and simply replace it with a modularized new component, directly in the field, in a minimum of time, to substantially reduce the complexity of the nozzle handling, and to significantly reduce the amount of time involved in servicing such a product.

The assignee's U.S. Pat. No. 5,562,133, shows another dispensing nozzle, and how all of the individual parts that make up the operating components for the shown nozzle, such as the poppet valve 20, and the automatic shutoff assembly 70, are located within the nozzle structure, as shown assembled. The assignee's U.S. Pat. No. 6,394,139 shows how an elliptical expansion plug has been applied to a universal nozzle casting body, so as to facilitate its servicing when it is taken apart, or even when the nozzle is initially assembled, during its building. Finally, the assignee's U.S. Pat. No. 6,585,014 shows an easy opening dispensing nozzle, but more specifically pertains to a novel lever assembly that regulates the flow of the fuel through the nozzle.

The current disclosure is designed to significantly improve upon the structure of the various components that make up the assembled dispensing nozzle, and more particularly to modularize the various operative components, so that they can be easily removed from the nozzle, replaced with a new like modular component, to greatly facilitate and reduce the amount of time involved in servicing of a dispensing nozzle in the field.

SUMMARY OF THE DISCLOSURE

This disclosure relates primarily to a dispensing nozzle, as previously alluded to, and more particularly involves the modularization of select operating components for a dispensing nozzle, so that the mod units, as a whole, can be easily removed, and replaced, during servicing, all of which may take place within the field.

Anyone familiar with dispensing nozzles knows that the nozzle is made up of nozzle housing, having at its frontal end and applied thereto its dispensing spout, held to the housing body by means of gland, and retention nut, which rigidly affixes the spout to the nozzle, during assembly, and for usage. Such a nozzle body also includes an inlet, at its back end, normally at the rear end of the portion of the nozzle that is grasped and held by the hand, in preparation for dispensing. Furthermore, the nozzle body includes a flow path there through, which is blocked, during shutoff, by means of the poppet valve part. It is known in the art that such poppet valves include a valve that seals internally of the nozzle body, to prevent the further flow there through, and the poppet valve is normally held into tight closure position by means of the poppet spring. And, to attain an operating opening of the poppet valve, when fluid is to be dispensed, a valve stem extends downwardly from the poppet valve, and is contacted by the operating lever for the nozzle, which when the hand lever is actuated and raised, the poppet stem biases against the force of the poppet spring, to allow for an opening of the main poppet valve for the nozzle, providing for the dispensing of fluid. Furthermore, since nozzles of these type currently are constructed of rather sophisticated technology, containing many, many operating parts, there is also an automatic shutoff means provided within the nozzle housing body, and that shutoff means operates in accordance with the various vacuums generated within the nozzle, during the flow of fluid through its housing, and which vacuums operate upon the shutoff means diaphragm, to provide for release of the automatic shutoff plunger, which provides for a lowering of the hand operating lever, which provides for a shutoff of the poppet valve, to curtail further flow of fluid through the dispensing nozzle.

The current disclosure, and what are believed to be its improved features, provides a nozzle that has the unique ability to remove modular cartridges from the functional areas of the nozzle for their ease of cleaning, replacement, and servicing, particularly when dispensing different or alternative fluids. Thus, with a modularization of the poppet valve assembly, into a cartridge configuration, this disclosure provides for the ability to remove the same by simply making a minor turn of the poppet valve retaining cap, so that the entire poppet valve assembly can be pulled upwardly, and out of the housing body, and a new modular cartridge for a poppet valve simply inserted therein, which greatly expedites the servicing of the poppet valve component of the dispensing nozzle.

Another advantage is to provide means for holding the spout assembly, as previously identified, with a unique spout nut that requires only an approximate quarter turn for its removal, and separation of the spout from the nozzle body housing, when the spout needs to be replaced or serviced.

Another advantage is the modularization of the design of the automatic shutoff means, and its diaphragm assembly, so that once the diaphragm cap is removed the entire diaphragm and plunger assembly as a unit can be removed, for immediate servicing, or replacement with a new modularized unit, furnishing a quick and expedited servicing of the nozzle, at this location of its component assembly, as required. Thus, it is the design of the modular cartridge components that facilitate their ease of removal, and replacement, when servicing, in the field, as required.

Another benefit is the capability of holding the plunger spring to the vacuum cap and the diaphragm assembly to assist with its assembly and disassembly, during servicing.

Another benefit of this disclosure is that the poppet structure, and the venturi for the nozzle, is combined into the same area to facilitate its modularity.

Finally, the hand guard as assembled with its binding post fasteners assists with the ease of assembly, and disassembly, during servicing, of the hand operating lever, even in the field. This has not been capable of consistent performance, previously, and quickly by a service man, at the site of servicing of a nozzle at a service station or other location.

It is, therefore, the principal object of this disclosure to provide a unique dispensing nozzle, where several of its operating components are modularized, can be removed intact, and replaced by a new mod component, for servicing directly in the field.

Another object of this disclosure to provide a dispensing nozzle where its various operating components are of a modularized assembly, and therefore, these various components can be assembled separately, as both at the plant, and simply added into the nozzle in the field, to greatly facilitate and expedite the assembly of a new nozzle, even at the manufacturing plant, at the site of its assembly and construction.

Another object of this disclosure is to provide components for fluid dispensing nozzle that have been well thought out as modularized of assembly, and can be applied or removed intact, when the nozzle is being manufactured, or serviced.

These and other objects may become more apparent to those skilled in the art upon review of the summary of the disclosure as provided herein, and upon undertaking a study of the description of its preferred embodiment, in view of the drawings.

DESCRIPTION OF THE DRAWINGS

In referring to the drawings,

FIG. 7 shows the poppet cap being removed from the nozzle housing body in the vicinity of the location of the poppet valve therein;

FIG. 8 provides a top view of the poppet cap of FIG. 7;

FIG. 9 shows a sectional view of the poppet cap taken along the line 9-9 of FIG. 8;

FIG. 10 shows a side view of the poppet cap;

FIG. 11 shows a side view of the poppet cap as it has been quarter turned from the view of the poppet cap in FIG. 10;

DESCRIPTION OF THE PREFERRED EMBODIMENT

Figure 1:
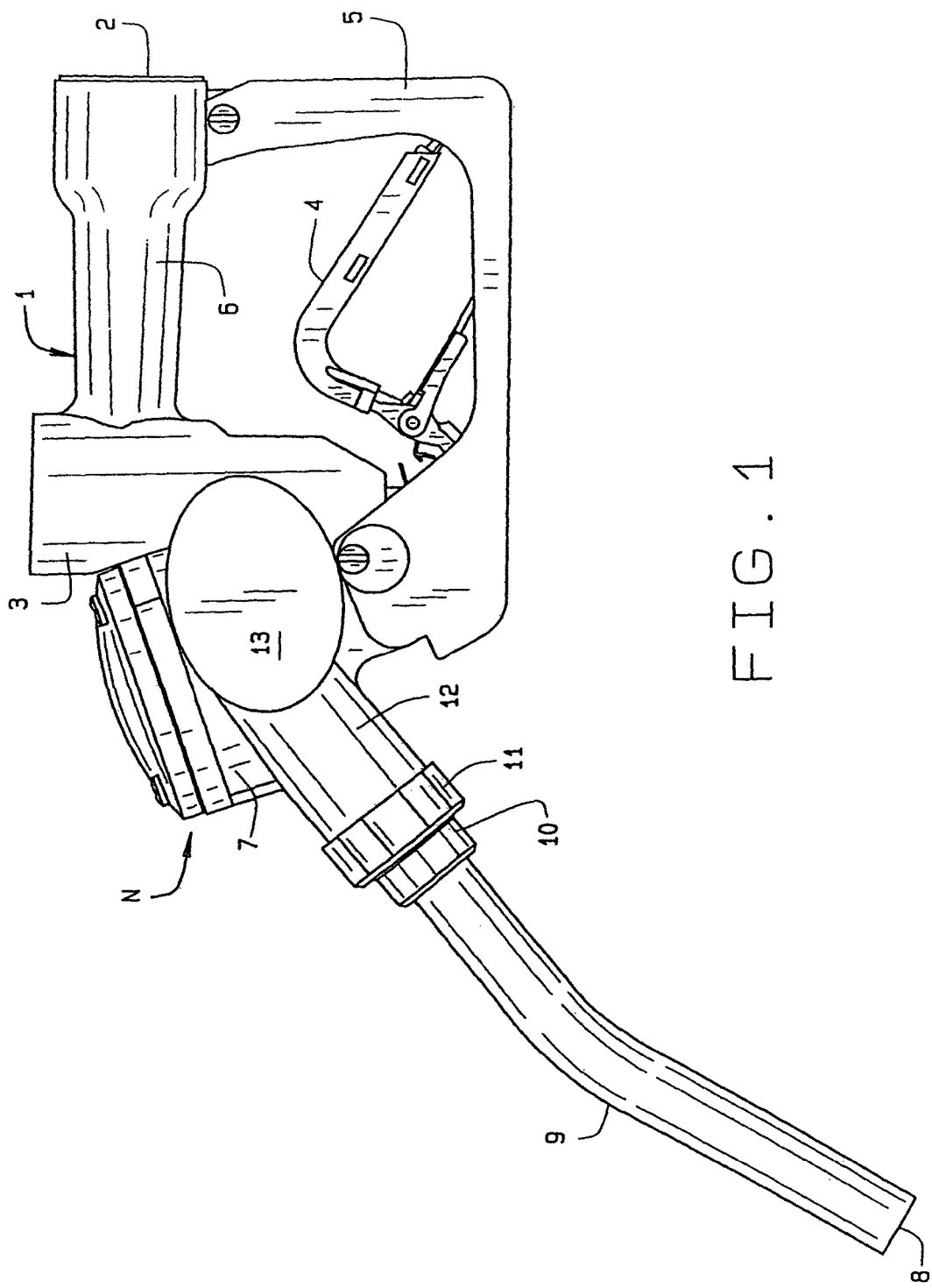
FIG. 1 provides a side view of the assembled dispensing nozzle of this disclosure.

In referring to the drawings, and in particular FIG. 1, a dispensing nozzle, as modified for the construction and installation of the modularized components assembled dispensing nozzle of this disclosure, is shown at N. The nozzle, as previously summarized, includes a nozzle housing body 1, which includes it back end as at 2, which is normally threaded internally, and to which the dispensing hose through its swivel connector attaches therewith, in a fluid sealed relationship. The nozzle body includes an integral upright segment 3 and it is within this segment that the poppet valve assembly locates, and which provides for the shutoff of the nozzle when dispensing is completed, or which can be elevated, to open the flow passage there through, so that fluid may traverse through the nozzle, for dispensing into the fill pipe of an automobile or other fluid receiving container. An operating hand lever 4 pivotally connects within the lever guard 5 and upon grasping the handle body portion 6 of the nozzle body, with the hand, and extending the fingers around the lever 4, it can be raised, for opening the main poppet valve for the nozzle, when dispensing is to commence. Forwardly of the poppet valve portion of the nozzle is the automatic shutoff integral casing 7 for the nozzle, and it is herein that the diaphragm and the automatic shutoff means for the nozzle is provided, so as to furnish an instantaneous shutoff to the flow of fluid through the nozzle, when the fluid tank and the fill pipe have been filled with fluid, and the fluid blocks the tip end 8 of the spout 9, as is well know in the art. The spout 9 is connected by means of the spout gland 10 and the spout retaining nut 11 to the integral frontal part of the nozzle housing 12 so as to complete the structure of the entire nozzle, and its integral components, into an operating dispensing nozzle. As shown in this model for the nozzle, is the elliptical expansion plug 13, which allows the nozzle to be converted into different styles of dispensing nozzles, so that one casting can be used as a universal housing for the variety of nozzles that are fabricated, for dispensing select styles of fluid to the trade.

Figure 2:
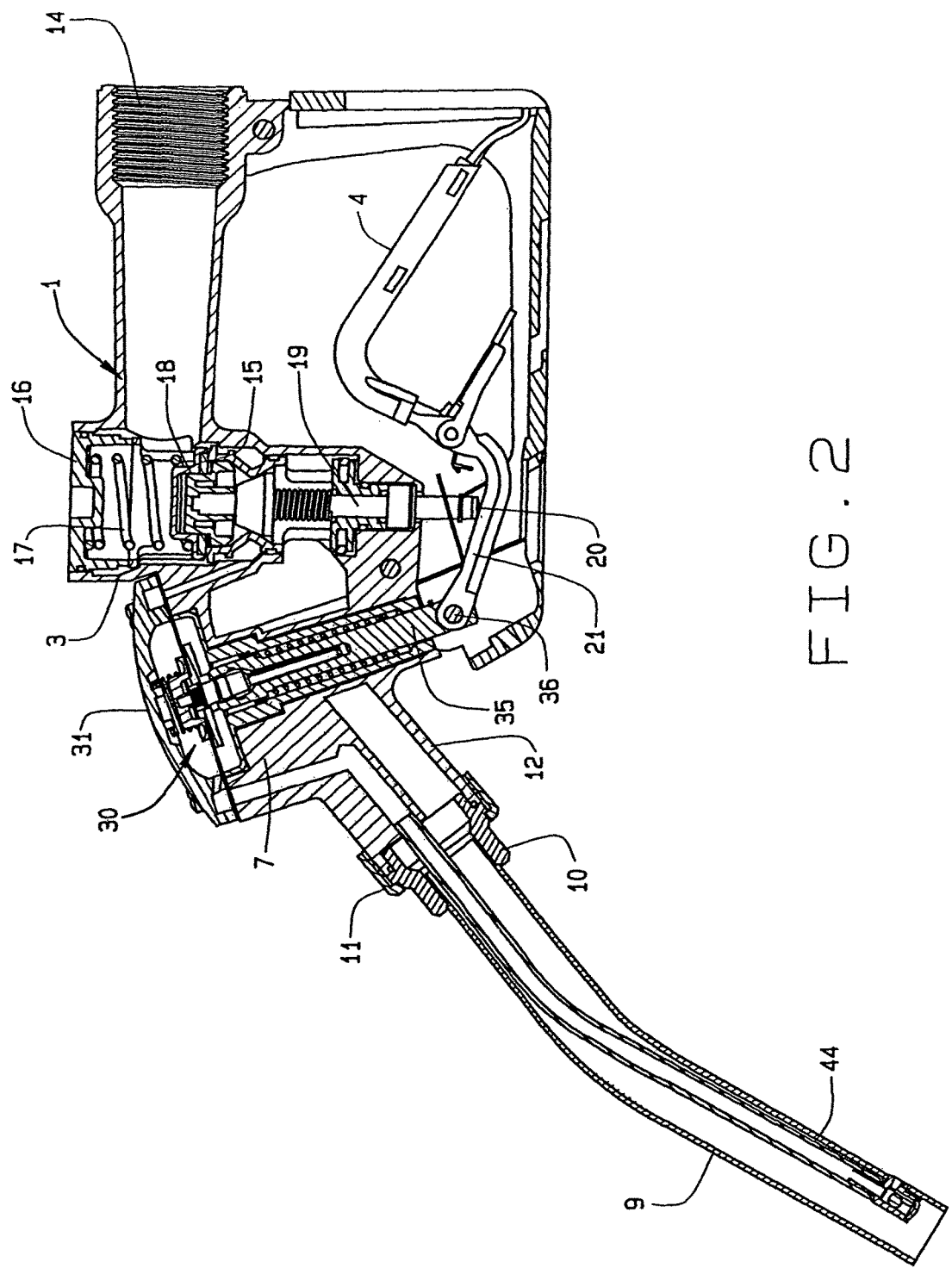
FIG. 2 provides a sectional view, along the length and through the center of the nozzle, showing its various operating components, the sectional view being taken of the nozzle as disclosed in FIG. 1.

As to be seen in FIG. 2, which is a sectional view throughout the length of the shown dispensing nozzle of FIG. 1, the nozzle body 1 has its threaded means 14 provided at its back end, as previously described, and the poppet valve assembly, as noted at 15, is embodied within the poppet valve portion 3 of the housing, as to be noted. A poppet cap 16 threadidly engages within the poppet housing 3, at its upper end, and provides the means for biasing against the poppet spring 17 which forcefully presses down on the poppet seal holder 18 to normally maintain the poppet valve 15 in its closed position, as shown in FIG. 2, as noted. As to be seen, the poppet stem 19 locates upwardly within the poppet 18, while at the bottom end 20 the stem 19 biases against the operating lever 4, at the vicinity of its forwardly extending end 21, as to be noted. Thus, when the operating lever 4 is raised, the stem 19 is raised upwardly, by the lever pushing against the bottom end 20 of said stem, and forces the poppet holder or hat 18 and its valve 15 to rise upwardly; this allows fluid to pass through the flow path of the nozzle, on its way towards the spout 9.

Figure 3:
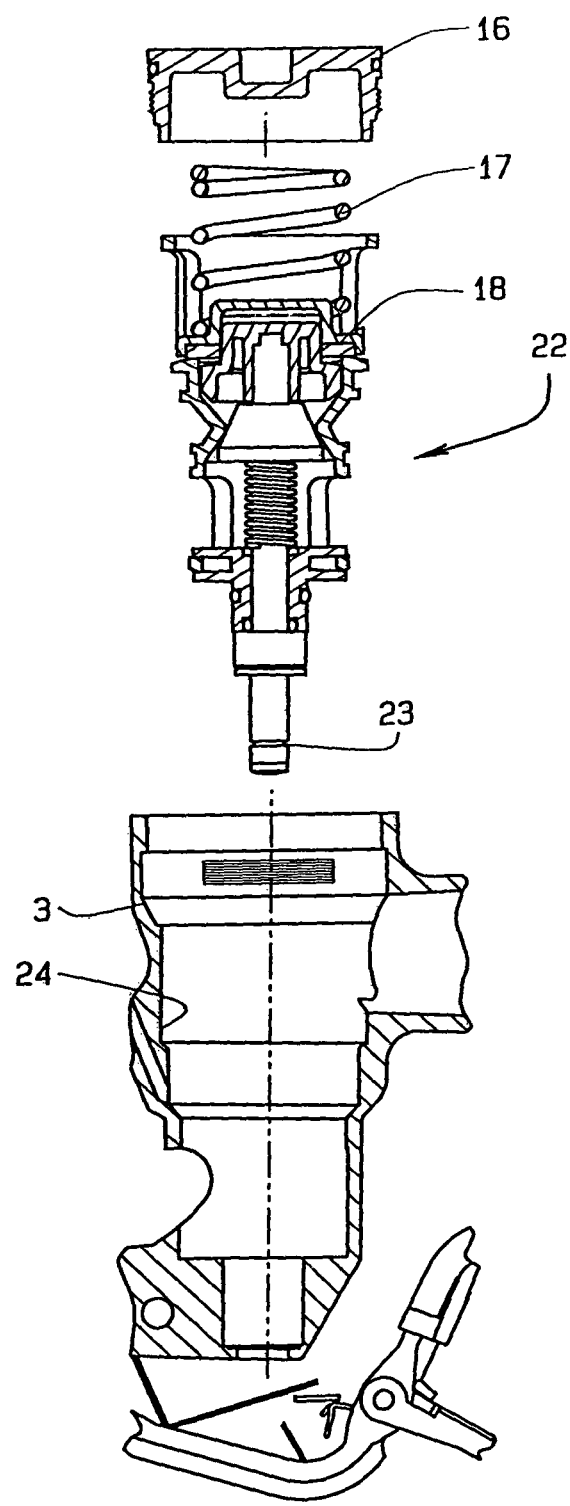
FIG. 3 shows an exploded view of the modularized poppet component being inserted or removed from the nozzle housing body during its assembly or servicing.

What is unique, though, about the structure of the specific nozzle as shown and described herein, and as to be seen in FIG. 3, the entire poppet valve assembly 22, as to be noted, has been modularized, once its cap 16 has been removed, and, if necessary, with its retainer latch pin which normally locates within the lower groove 23 is removed, the entire modularized poppet assembly, with its cap 16 can raise upwardly, and be easily removed from the formed poppet housing 24 of the poppet housing structure 3 as described, and as can be noted. Thus, it is a very easy function for the service person in the field, to simply remove the retainer latch as 23, lift the poppet cap 16 by threadily unthreading it from the nozzle body, wherein the poppet spring 17, in the poppet valve structure 18, can be readily removed, and replaced, by a new mod unit, directly in the field. It is to be noted that the entire mod unit for the poppet assembly is tapered from its top to the bottom to ease its removal or installation during nozzle services. This may take a matter of minutes to complete that servicing function, which heretofore, required an entire disassembling of the nozzle, a removal of its component parts structured into the poppet valve assembly, which normally could not be done in the field, and had to be performed back at the manufacturing plant, where the nozzle is brought to for rebuilding.

Another means for engagement of the poppet cap 16, through its threads 25, as to be noted, is shown in FIG. 7, and its engagement with the sectionalized threads 26 within the poppet structure 3 of the housing, discloses a uniquely designed thread pattern having spaced gaps, as at 27 and 28 provided between sections of the shown threads, which allows for the poppet cap to simply undertake a quarter turn, in order to achieve its removal from the nozzle housing, during a servicing function. Hence, this drastically reduces the amount of time involved in having to service the nozzle, particularly of this poppet structure, in the field. A socket, as shown at 29, is provided within the upper exposed surface of the poppet cap 16, and then a tool or wrench can be applied therein, turned for a quarter turn, which allows the entire cap to be removed, for prompt removal of the poppet spring, and the modularized poppet valve assembly, from the nozzle housing, for replacement.

Figure 4:
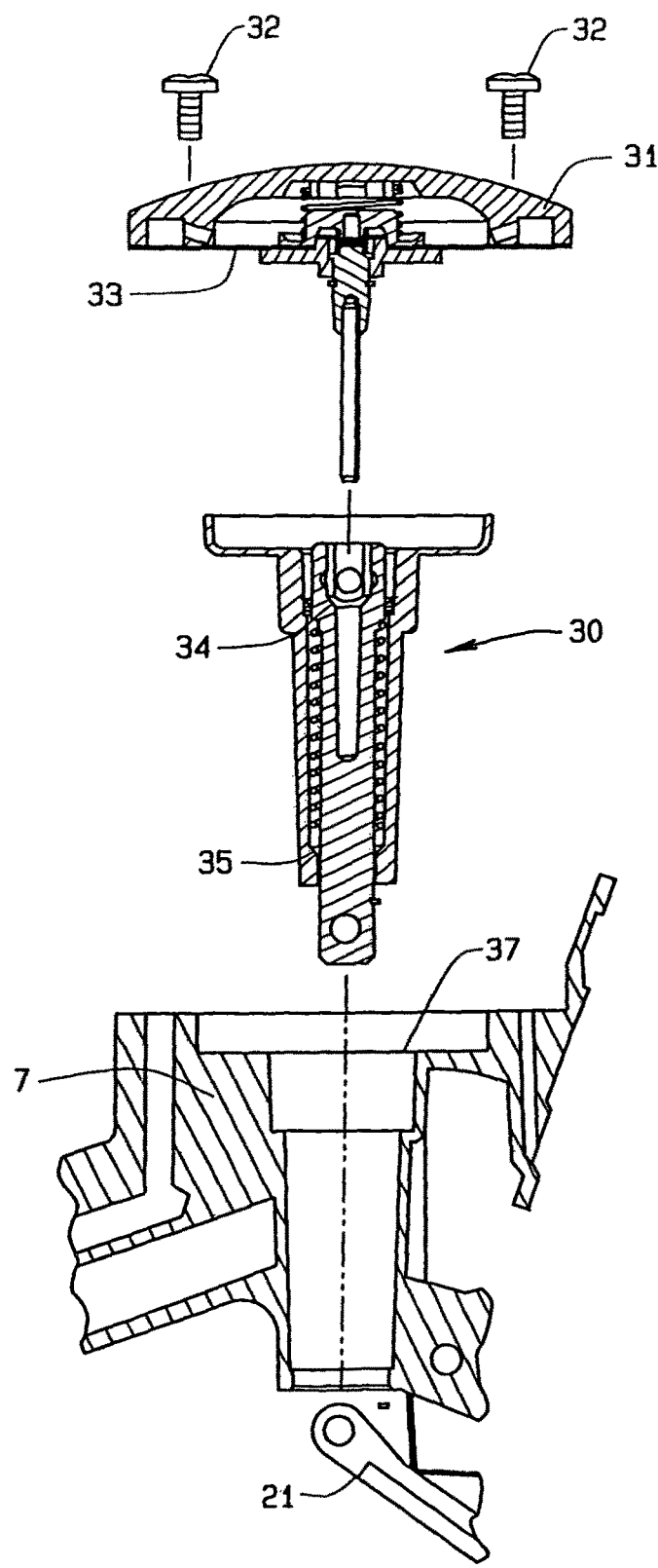
FIG. 4 shows an exploded view of the automatic shutoff diaphragm and its component assembly in the process of being applied, or removed, from the nozzle housing body during its assembly or servicing.

As previously stated, the automatic shutoff part of the housing, as at 7, is shown forwardly of the poppet valve assembly area, and it is within this portion of the nozzle that the automatic shutoff means 30 locates. As can also be seen in FIG. 4, the shutoff means includes its cap 31, that threadidly engages by means of fasteners, as at 32, to the nozzle body, and provides for coverage eternally thereof of the entire automatic shutoff unit 30, in its modular form, as to be noted. The diaphragm for the automatic shutoff is noted at 33. This diaphragm assembly, with the cap, cooperates with the latch pin 34 that holds the plunger 35 fixed in position and held upwardly within the assembly structure, as known in the art, to allow dispensing of fuel to continue, until such time as the tip of the nozzle spout 9 becomes emersed in fluid as it fills the tank and fill pipe for the vehicle or fluid receiving container, which breaks the generated vacuum, and pulls the latch pin upwardly, for allowing the plunger 35 to shift downwardly to release the handle lever 4 to drop downwardly, allowing the poppet to lower within the nozzle housing body, and to shutoff the further flow of fluid through the dispensing nozzle. Many of these components are standard in the industry, with the exception that they have been modified to provide for their structuring into a modularized type of component, so that once the shutoff cap 31 is removed, through removal of its fasteners 32, and the hand lever pin 36 is removed, the entire automatic shutoff means 30 can be shifted upwardly, pulled out of the nozzle housing, and be immediately replaced with a new automatic shutoff diaphragm unit, and allow the nozzle to be immediately put back into service, as can be understood. Note that the entire unit has a tapered configuration, to ease its rebuilding and replacement. All of this can be done by the service person in the field, at the service station, or at any other location where fluid is being dispensed, without requiring the nozzle to be removed, and shipped back to the manufacturing plant, for rebuilding. Thus, the modularized component for the diaphragm automatic shutoff means 30, as to be seen, is of an integral structure, and can be lifted free from the nozzle body 7 as noted in said FIG. 4.

Thus, this provides a second part of the modularized components for the dispensing nozzle of this disclosure, which can facilitate servicing of the nozzle, in the field, in a most prompt, efficient, and facile manner. The service man does not need to pick apart the entire structure of the automatic shutoff unit 30, in the field, and separate all of its many functional components, but rather, can simply place the entire new modular unit, intact, directly into the cavity 37 of the nozzle body 7, apply the shutoff cap 31 in place, fasten it into closure, and reapply the pivot pin 36, for the hand lever, as noted. This provides a second form of modularized componentry for the dispensing nozzle of this disclosure.

Figure 6:
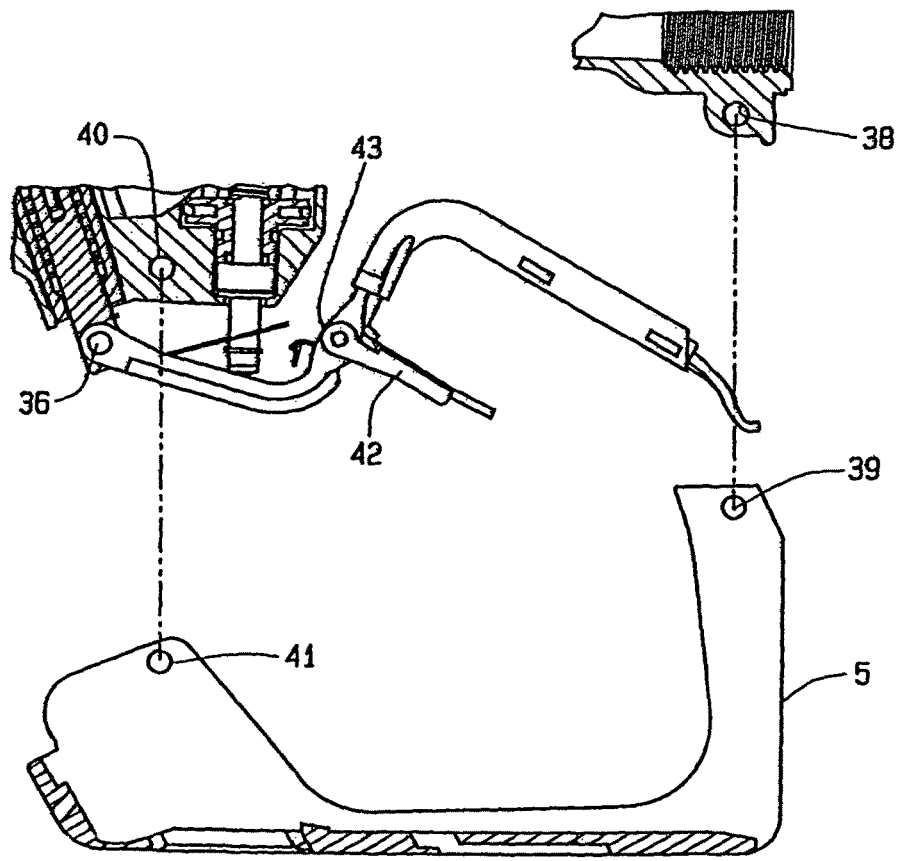
FIG. 6 discloses how the hand operating lever assembly for the fuel dispensing nozzle can be removed intact, as a modularized component.
Figure 12:
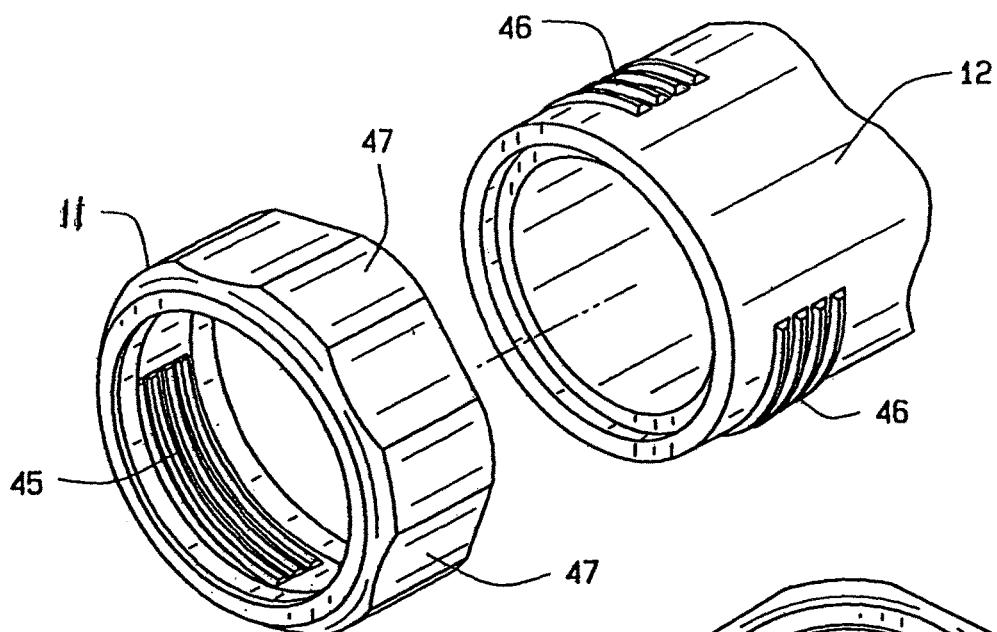
FIG. 12 shows the retaining nut as removed from the front of the nozzle housing body.
Figure 13:
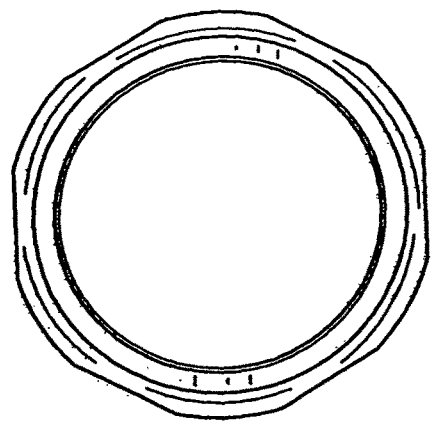
FIG. 13 is a front view of the retaining nut of FIG. 12.

As can further be seen in the structure of the dispensing nozzle of this disclosure, the operating hand lever 4 connects at two locations with the nozzle. The initial one is the biasing of the bottom end 20 of the poppet stem 19 against the forward lever component 21, and secondly, the use of the pivot pin 36, which holds the front of the hand lever pivotally to the bottom of the automatic shutoff plunger 35, as previously explained. As can also be seen in FIG. 6, even the hand lever 4 can be readily removed from the structure of the dispensing nozzle, with only a few minor disengagements. For example, the removal of a pin at the upper back part of the hand guard 5, where the pin locates through the pair of apertures 38 and 39, and the removal of a pin that locates through the aligned apertures 40 and 41, the latter being located at the upper front of the hand guard 5, allows for the hand guard to be removed. Then, if the operating hand lever 4 has been damaged, or worn-out, a simple removal of its pivot pin 36 provides for a release of the operating handle 4, and its immediate replacement, with all of its various components that are attached thereto, such as the lever 4, its latch clip 42, and the various anti-rattle springs and clips, as noted at 43, all may be replaced, as a modular type component, when any part of it becomes worn-out, or soiled to the extent that it must be replaced. Once again, this is a simple procedure to be preformed by the service person in the field, which makes this nozzle much more customer friendly, able to be immediately serviced in the field, and not require the customer to buy a new or rebuilt nozzle, at a substantial savings in cost and usage. This provides a third type of modular componentry for the dispensing nozzle of this disclosure.

Figure 5:
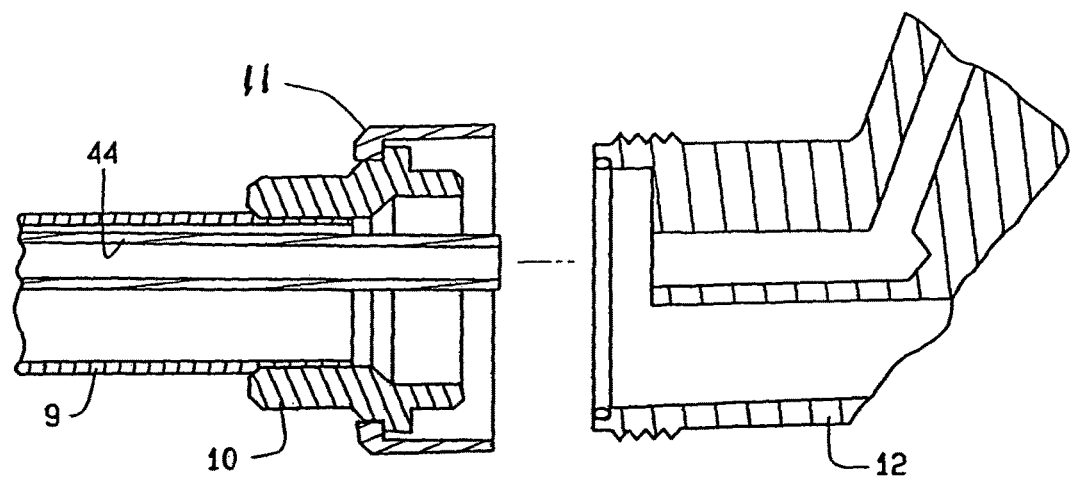
FIG. 5 shows a new style of spout, gland, and retaining nut as removed from the front of the nozzle housing body.
Figure 14:
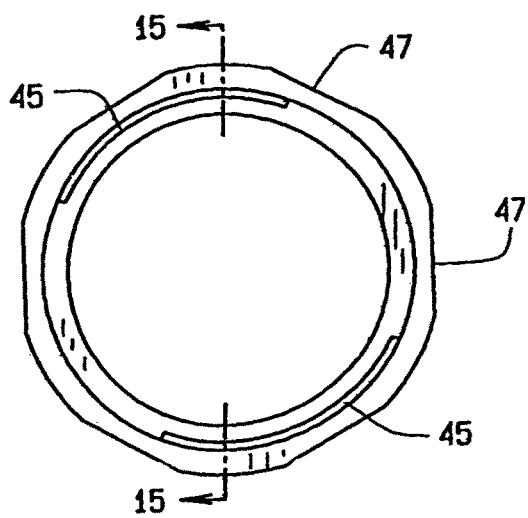
FIG. 14 is a back view of the retaining nut for the spout and showing the spaced segments of threads applied internally thereof.
Figure 15:
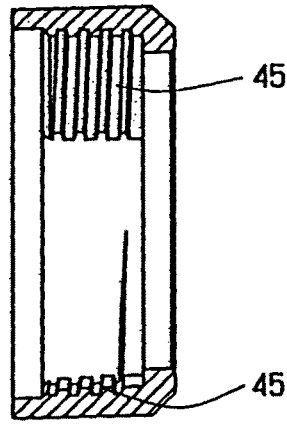
FIG. 15 provides a sectional view of the retaining nut taken along the line 15-15 of FIG. 14.

Another improvement to the structured assembly of the dispensing nozzle of this disclosure, and which renders it efficient in its servicing particularly within the spout area of the nozzle, can also be seen in FIG. 2. As noted, the spout gland 10 connects upon the upper end of the spout, and seals therewith, and is held in position rigidly affixed to the integral frontal end of the nozzle housing 12 by means of the spout retaining nut 11. These elements can also be seen in greater detail in FIG. 5. The tube 44 is the conventional vent tube that extends to the forward end of the spout, as can also be seen in FIG. 2, which cooperates to provide for the automatic shutoff of the nozzle when the tank becomes filled. The retaining nut 11 can be seen in greater detail in FIGS. 12 through 15, and said nut includes segments of threads 45 both extending approximately, or less, 90.degree. internally of the retaining nut, as can also be seen in FIG. 14. In addition, the threaded end of the nozzle body 12 includes segments of threads, as at 46, that extend also approximately 90.degree., or less, around the outer circumference of the shown body 12. Hence, when the retaining nut, as affixed upon the spout gland 10, and retains the spout 9 herein, said retaining nut is threadily engaged upon the nozzle body 12, with the nut 11 being turned approximately a quarter turn, to provide for a very firm interconnection between the retaining nut, and the nozzle body, thereby holding the spout fixedly in place, upon the frontal portion of the nozzle, as to be noted in FIGS. 1 and 2 of the disclosure. Obviously, the outer surface of the retaining nut 11 includes a series of lands, as at 47, to accommodate a wrench, that allows for the forceful application of the retaining nut in place, when the spout is being affixed to the front of the nozzle body, or to be turned counterclockwise, for its removal, when it is necessary to remove and replace the spout from the structure of the dispensing nozzle. Hence, this provides another facile manner in which the components of the dispensing nozzle can be immediately removed, in the field, and readily replaced, within a minimum of time and effort.

Thus, the concept of this disclosure is to transfer the servicing of various operating components of a dispensing nozzle, from the manufacturing plant, as where nozzles are normally manufactured or rebuilt, out into the field, at the location of their usage, usually at a service station, with a minimum of effort on the part of the service person. Furthermore, this allows the service person to remove the various modular cartridges from the functional areas of the nozzle, for ease of their cleaning or replacement, particularly when the nozzle may be used for dispensing alternate fluids, which may require different type of seals, and o-rings in the operating structures of the components, all of which can be done directly in the field, when a service station may be switching over from dispensing routine fluids, or for use for dispensing fluids that may be used on the farm, or elsewhere. Thus, the nozzle is designed for accommodating its revision and modification directly at the site of its usage, this makes the nozzle much more compatible for accommodating a variety of fluids, and to be modified in situ, when the owner selects the type of fluid to be dispensed, requiring the nozzle to be modified accordingly, to accommodate such different usage.

Variations or modifications to the subject matter of this disclosure may occur to those skilled in the art upon review of the development as described herein. The various components of the nozzle, and their embodiment into modular form, may be considered by others upon review of the disclosure as provided herein. Such variations, if within the spirit of this disclosure, are intended to be the encompassed with the scope of any claims to patent protection that may be provided herein. The specific structure of the nozzle, and its various components, as described in the application, and as depicted in the drawings, are set forth for illustrative purposes only.

We claim:

1. A modularized components assembled dispensing nozzle comprising:

a nozzle housing body having a flow path there through for the flow of fluid for dispensing to a vehicle or fluid accepting container, the nozzle housing body having a back end having a connector for attachment of a dispensing hose thereto, and the nozzle housing body having a front end;

a poppet housing formed in the nozzle housing body;

a poppet valve assembly for insertion into the poppet housing;

a poppet cap for being threaded into the poppet housing and fitting within the poppet housing and the poppet cap being flush with the poppet housing for containing the poppet valve assembly therein;

an automatic shutoff assembly for insertion into the nozzle housing body;

a cap for covering the automatic shutoff assembly with the cap being fastened to the nozzle housing body;

a spout connected to the front end of the nozzle housing body by use of a retaining nut, the spout for delivery of fluid there through and into a fill pipe of the vehicle or fluid accepting container;

the poppet valve assembly providing for opening of the flow path for allowing fluid to flow through the nozzle housing body for delivery, the automatic shutoff assembly providing for the automatic shutoff of the poppet valve assembly when a fluid tank is filled with delivered fluid, the entire poppet valve assembly being modularized and having a narrowing taper from top to bottom to provide for the entire poppet valve assembly to be delivered into the poppet housing for installation, during assembly or servicing in the field of said dispensing nozzle, or to provide for removal of the poppet valve assembly by removal of the poppet cap during servicing and the entire automatic shutoff valve assembly being modularized and having a narrowing taper from top to bottom to provide for the entire automatic shutoff valve assembly to be delivered into the nozzle housing body for installation, or to provide for removal of the entire automatic shutoff assembly by removal of the cap during servicing in the field; and said nozzle having an elliptical expansion plug provided along its side, and overlapping the location of the poppet valve assembly and the automatic shut-off valve assembly, such that when said plug is removed, the nozzle may be converted to different styles of dispensing nozzles in preparation for usage.

2. The modularized components assembled dispensing nozzle of claim 1 wherein the retaining nut of the spout further comprises a series of internal segments of threads for securing the spout to the front end of the nozzle housing body, the series of internal segments of threads being arranged diametrically within the retaining nut, the front end of the nozzle housing body having segmented threads diametrically arranged upon an outer surface of the nozzle housing body whereby upon the connecting of the spout by use of the retaining nut to the nozzle housing body the retaining nut threads locate immediately the housing body threads, and within approximately a quarter turn provides for rigid connecting of the spout to the nozzle housing body during installation.

3. The modularized components assembled dispensing nozzle of claim 2 wherein the retaining nut further comprises a series of lands for accommodating the application of a tool to provide for the fastening or removal of the retaining nut from the nozzle housing body during installation or removal of the spout.

4. The modularized components assembled dispensing nozzle of claim 1 wherein the automatic shutoff assembly is entirely modularized, having its reduced tapering configuration along its length to accommodate its installation within the nozzle housing body during assembly or servicing.

5. The modularized components assembled dispensing nozzle of claim 1 wherein the poppet cap comprises a series of segmented threads, the threads being arranged diametrically spaced from each other upon a downwardly extending sleeve of the poppet cap, the poppet housing having corresponding threads placed diametrically from each other and arranged offset from the cap threads, whereby upon application of the poppet cap into the poppet housing a quarter turn of the cap provides for a locking of the poppet valve assembly within the poppet housing.

* * * * *